(12) United States Patent
Honjo et al.

(10) Patent No.: US 7,773,720 B2
(45) Date of Patent: Aug. 10, 2010

(54) UNIT FOR X-RAY CT IMAGING AND X-RAY IMAGING APPARATUS

(75) Inventors: Makoto Honjo, Kyoto (JP); Takahiro Yoshimura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 28 days.

(21) Appl. No.: 11/918,197

(22) PCT Filed: Apr. 11, 2006

(86) PCT No.: PCT/JP2006/307663

§ 371 (c)(1),
(2), (4) Date: Oct. 10, 2007

(87) PCT Pub. No.: WO2006/109802

PCT Pub. Date: Oct. 19, 2006

(65) Prior Publication Data

US 2009/0052616 A1 Feb. 26, 2009

(30) Foreign Application Priority Data

Apr. 11, 2005 (JP) .............................. 2005-113835
Apr. 12, 2005 (JP) .............................. 2005-115151

(51) Int. Cl.
*A61B 6/03* (2006.01)
*A61B 6/14* (2006.01)
*H05G 1/02* (2006.01)

(52) U.S. Cl. .............................. 378/19; 378/38; 378/39; 378/40; 378/189; 378/191; 378/197

(58) Field of Classification Search .................... 378/19, 378/38, 39, 40, 98.8, 189, 191, 196, 197
See application file for complete search history.

(56) References Cited

U.S. PATENT DOCUMENTS

| | | | | |
|---|---|---|---|---|
| 5,844,961 A * | 12/1998 | McEvoy et al. | ............ | 378/98.8 |
| 6,173,035 B1 | 1/2001 | Tachibana | | |
| 6,289,074 B1 | 9/2001 | Arai et al. | | |
| 6,493,415 B1 * | 12/2002 | Arai et al. | ....................... | 378/4 |
| 6,584,171 B2 * | 6/2003 | Suzuki et al. | .............. | 378/98.8 |

(Continued)

FOREIGN PATENT DOCUMENTS

DE    197 54 670    10/1998

(Continued)

*Primary Examiner*—Allen C. Ho
(74) *Attorney, Agent, or Firm*—William L. Androlia; H. Henry Koda

(57) ABSTRACT

A unit for X-ray CT imaging to be set in a panorama X-ray imaging apparatus having a cassette holder has a digital sensor cassette for CT imaging to be set in the cassette holder, includes a two-dimensional X-ray detector for acquiring X-ray projection data for CT imaging of an object, and a controller for controlling a timing of X-ray CT imaging, a radiation field of X-ray beam generated by the X-ray detector, and the rotary device. Alternatively, the unit has the digital sensor cassette for X-ray CT imaging, an image reconstructor which calculates to convert the X-ray projection data obtained with the two-dimensional X-ray detector to a distribution of X-ray absorption coefficients of the object and creates tomographic image data of sections of the object, and an image processor which sends and receives signals for X-ray CT imaging between the X-ray detector and the image reconstructor when the digital sensor cassette for CT imaging is set in the cassette holder.

14 Claims, 6 Drawing Sheets

U.S. PATENT DOCUMENTS

| | | | |
|---|---|---|---|
| 7,236,563 B2 * | 6/2007 | Sa et al. | 378/39 |
| 7,315,608 B2 * | 1/2008 | Sa et al. | 378/38 |
| 7,322,746 B2 * | 1/2008 | Beckhaus et al. | 378/205 |
| 7,347,622 B2 * | 3/2008 | Sadakane et al. | 378/197 |
| 7,424,091 B2 * | 9/2008 | Park et al. | 378/39 |
| 7,486,759 B2 * | 2/2009 | Suzuki et al. | 378/4 |
| 7,577,232 B2 * | 8/2009 | Tachibana et al. | 378/39 |

FOREIGN PATENT DOCUMENTS

| | | |
|---|---|---|
| DE | 103 13 110 | 10/2004 |
| JP | 9-135829 | 5/1997 |
| JP | 11-104127 | 4/1999 |
| JP | 2000-139902 | 5/2000 |
| JP | 2001-190550 | 7/2001 |
| WO | WO 2004/084728 | 10/2004 |
| WO | WO 2004/084729 A1 * | 10/2004 |

* cited by examiner

Prior Art

UNIT FOR X-RAY CT IMAGING AND X-RAY IMAGING APPARATUS

TECHNICAL FIELD

The invention relates to medical X-ray imaging for dentistry, otorhinolaryngology and the like.

BACKGROUND ART

Various medical X-ray imaging apparatuses are used according to various purposes. For example, apparatus for dentistry includes a panorama X-ray imaging apparatus for imaging a dental arch and thereabout at the same time, a cephalo imaging for imaging an entire head of a patient for orthodontics, and an X-ray computed tomography (CT) imaging apparatus for imaging a part of a dental arch with an X-ray cone beam. Linear tomography imaging is also possible for a section of a dental arch.

For the various types of X-ray imaging apparatuses, various X-rays are used such as a long radiation field for panorama imaging or the like, a wide radiation field for cephalo imaging and a cone beam for CT imaging. Further, various sensors such as an X-ray film, an X-ray image intensifier, and a two dimensional sensor including a CCD sensor, a MOS sensor or the like are used for the apparatuses. The specifications of the X-ray source and the X-ray sensor and the rotation condition depend on the type of imaging.

For example, in panorama X-ray imaging, the positions of the X-ray source and the X-ray sensor are moved along a trajectory so that a narrow X-ray beam always radiates the dental arch in the normal direction and detects the beam with an X-ray film or an X-ray digital sensor. In X-ray CT imaging, for example, an X-ray beam radiates an object while an arm which holds an X-ray generator and an X-ray detector opposing to each other is rotated, and a projection of the beam is detected with a digital sensor.

It is conventional to modify an existing X-ray imaging apparatus to perform various types of imaging. For example, it is proposed to enable panorama imaging and linear tomography imaging by changing from an X-ray digital sensor cassette to an X-ray film and vice versa. In an X-ray panorama imaging apparatus described in Japanese patent laid open Publication JP-A H9-135829/1997, in order to decrease a change time and to shorten a time for X-ray tomography imaging for smooth running and acceleration of a medical process, in an X-ray panorama imaging apparatus described in JP-A H9-135829, an X-ray film cassette and a digital X-ray sensor cassette are held in the same cassette holder, and one of them is set at the central position, while the other is retracted. Thus, one of them can be set fast manually or automatically. However, as the structure of an X-ray detector becomes complicated, and an exclusive X-ray detector is required instead of an X-ray detector for a general film cassette. Then, in a panorama X-ray imaging apparatus proposed in Japanese patent laid open Publication JP-A H11-104127/1999, an apparatus for a film cassette is modified a little to use a digital sensor cassette. When a digital sensor cassette is set instead of a film cassette, an imaging mode for the digital sensor cassette is selected automatically, and imaging conditions for the mode are set. Then an imaging is performed by supplying control signals to the digital sensor cassette.

In the above-mentioned various dental X-ray imaging apparatuses, panorama (and cephalo) imaging apparatuses are used widely. When a dentist observes a panorama X-ray photograph obtained with a panorama imaging apparatus and wants to have a tomography image on a part of the panorama view, the tomography image can be obtained if an X-ray CT imaging apparatus is available. However, because an X-ray CT imaging apparatus is expensive, it is not always possible for the dentist to use an X-ray CT imaging apparatus. Therefore, it is desirable that a simple modification of a panorama imaging apparatus makes X-ray CT imaging possible. However, because the specifications of X-ray detector and X-ray sensor, imaging conditions and the like are different among imaging types, simple replacement of X-ray sensor is not sufficient to implement various types of imaging.

DISCLOSURE OF INVENTION

It is an object of the invention to perform X-ray CT imaging easily based on an X-ray imaging apparatus for acquiring a panorama tomography image.

A first unit for X-ray CT imaging according to the invention to be set in a panorama X-ray imaging apparatus has a cassette holder wherein a film cassette including an X-ray film or a digital sensor cassette including an electric X-ray detector for acquiring a panorama image data is set. The panorama X-ray imaging apparatus has an X-ray generator, an X-ray detector including the cassette holder interposing an object and opposing to each other, and a rotary device which rotates the X-ray generator and the X-ray detector while keeping them opposing to each other and interposing the object, whereby a panorama tomography image of the object according to X-ray radiations from the X-ray generator. The unit includes a digital sensor cassette for CT imaging to be set in the cassette holder, including a two-dimensional X-ray detector for acquiring X-ray projection data for CT imaging of the object, and a controller for controlling a timing of X-ray CT imaging, a radiation field of X-ray beam generated by the X-ray generator, and the rotary device. Preferably, the first unit has a controller for controlling a timing of X-ray CT imaging, a radiation field of X-ray beam generated by the X-ray detector, and the rotary device, a image reconstructor which calculates to convert the X-ray projection data obtained with the two-dimensional X-ray detector to a distribution of X-ray absorption coefficients of the object and creates a tomographic image data of sections of the object, and an image processor which sends and receives signals for X-ray CT imaging between the X-ray detector and the image reconstructor when the digital sensor cassette for CT imaging is set in the cassette holder.

A second unit for X-ray CT imaging according to the invention to be set in a panorama X-ray imaging apparatus has a cassette holder wherein a film cassette including an X-ray film or a digital sensor cassette including an electric X-ray detector for imaging a panorama image is mounted. The panorama X-ray imaging apparatus has an X-ray generator, an X-ray detector including the cassette holder interposing an object and opposing to each other, and a rotary device which rotates the X-ray generator and the X-ray detector while keeping them opposing to each other and interposing the object, whereby a panorama tomography image of the object is acquired according to X-ray radiations from the X-ray generator. The unit has a digital sensor cassette for CT imaging to be set in the cassette holder, including a two-dimensional X-ray detector for acquiring X-ray projection data for CT imaging of the object, an image reconstructor which calculates to convert the X-ray projection data acquired by the two-dimensional X-ray detector to a distribution of X-ray absorption coefficients of the object and creates a tomographic image data of sections of the object, and an image processor which sends and receives signals for X-ray CT imaging between the X-ray detector and the image reconstructor when the digital sensor cassette for CT imaging is set in the cassette holder.

Preferably, in the first or second unit for X-ray CT imaging, a device for changing radiation field of X-ray beam generated by the X-ray generator is mounted for the two-dimensional X-ray detector at the side opposing the X-ray generator, and the device sets the radiation field for CT imaging when the digital sensor cassette for CT imaging is set in the cassette holder.

Preferably, the first or second unit for X-ray CT imaging has one of a switch, a jack for inserting a pin, a component to be engaged with a limit switch in the cassette holder, an IC tag, a bar code and an IC tip as a device for responding to the setting of the cassette.

Preferably, in the first or second unit for X-ray CT imaging, the two-dimensional detector is one of X-ray detectors and X-ray solid state imaging elements, including a MOS sensor, a CMOS sensor, a TFT sensor, an X-ray solid state imaging element and an FT sensor.

Preferably, in the first or second unit for X-ray CT imaging, the digital sensor cassette for CT imaging includes both of the two-dimensional X-ray detector for CT imaging and an X-ray detector for panorama imaging longer than the two dimensional X-ray detector. That is, the cassette has two types of two-dimensional X-ray detectors, and one of them can be set at an imaging position according to imaging mode.

An X-ray imaging apparatus according to the invention has a cassette holder wherein a film cassette including an X-ray film or a digital sensor cassette includingan electric X-ray detector for imaging a panorama image is mounted, an X-ray generator and an X-ray detector included in the cassette holder, interposing an object and opposing to each other, a rotary device which rotates the X-ray generator and the X-ray detector relative to the object while keeping them opposing to each other and interposing the object, and a unit for X-ray CT imaging according to the present invention, to be set instead of the film cassette or the digital sensor cassette.

ADVANTAGES OF THE INVENTION

It is an advantage of the invention that X-ray CT imaging is performed easily by changing a digital sensor cassette for CT imaging, an image reconstructor and a signal processor entirely, in a unit for X-ray CT imaging used for an X-ray imaging apparatus for panorama tomography images.

BEST MODE FOR CARRYING OUT THE INVENTION

Embodiments of the invention are explained below with reference to the appended drawings.

Figure 1:
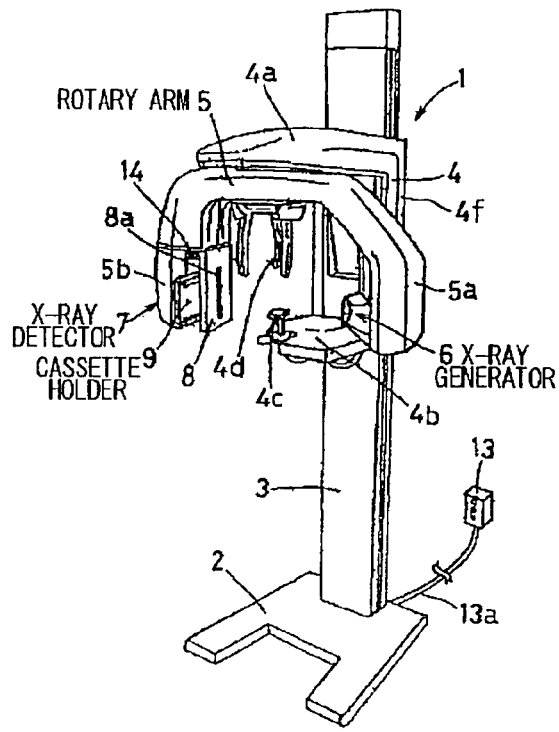
FIG. 1 is a perspective view of a panorama X-ray imaging apparatus.

FIG. 1 shows a panorama X-ray imaging apparatus. In a main body 1 of the apparatus, a vertical support 3 stands on a base 2, and a lift unit 4 is mounted to the vertical support 3 so as to move up and down. A rotary arm 5 is supported by the lift unit 4 so that it can rotate. The lift unit 4 has a support frame 4a and a patient frame 4b both extending horizontally, at a top end and a bottom end thereof. The support frame 4a includes an X-Y table movable in X and Y directions with step motors, and the rotary arm 5 is suspended from the X-Y table with a connection shaft and can be moved by the X-Y table in a horizontal plane freely. Alternatively, two arms connected like a drafter may be used instead of the X-Y table. The rotary arm 5 has a rotation mechanism for rotating the rotary arm 5 relatively to the support frame 4a. The mechanism can rotate the rotary arm 5 around a vertical line by moving the rotation center of the rotary arm 5 with the X-Y table. The rotary arm 5 extends downward at both ends 5a and 5b thereof. At one of the ends, an X-ray generator 6 including an X-ray tube is set, while at the other thereof, an X-ray detector 7 is set, opposing to each other in a horizontal direction. A housing of the X-ray generator 6 includes an X-ray tube, an X-ray shield plate having primary slits and an adjustment mechanism for changing the shape of the primary slits. The rotary arm 5 and the rotation mechanism are a part of a rotation means or a rotation device which arranges the X-ray generator and the X-ray detector to oppose to each other and to interpose an object and rotates them relative to the object while keeping them opposing to each other. Further, a remote control box 13 is connected via an operation cable 13a to the main body 1. It has a main switch for turning on or off the power supply and a switch for X-ray radiation.

The patient frame 4b has a chin rest 4c. A device 4d for fixing a patient's head is provided at the lower plane of the support frame 4a through the rotary arm 5, and a mechanism for position adjustment is also provided for the device 4d. Preferably, a mechanism for moving up and down the chin rest is also provided for the chin rest 4c. Further, an adjustment mechanism for tilting the chin rest 4c is also provided. By constructing the chin rest 4c movable as mentioned above, it is possible to adjust the tilt relative to the horizontal plane of the radiations for each of the imaging portions such as upper and lower jaws. It is also possible to set portions separated above and below, such as a jaw joint positioned above and a top of the lower jaw positioned below, at the center of radiation field.

The structures of the lift frame 4f and the patient frame 4b of the lift unit 4 are explained here which is moved up and down relative to the vertical support 3. In the example shown in FIG. 1, the lift frame 4f is moved up and down relative to the vertical support 3 according to the body size of a patient. Because the lift frame 4f and the patient frame 4b are formed as an integrated body, the X-ray generator 6 and the X-ray detector 7 are moved up and down with the patient frame 4b and the chin rest 4c. However, the patient frame 4b may be provided as a different component from the lift frame 4f which moves the X-ray generator 6 and the X-ray detector 7 up and down, so that the two frames 4b and 4f are moved relative to the vertical support 3 independently of each other. Further, the X-ray generator 6 may be moved up and down relative to the patient frame 4b or the chin rest 4c. Such examples are disclosed in Japanese Patent laid open Publication JP-A H7-275240/1995, wherein a component in correspondence to the patient frame 4b is called as "patient frame", and a component in correspondence to the lift unit 4 or the lift frame 4f is called as "main body for moving up and down". An object for the up and down movement and the tilting is to widen an area which can be imaged and to adjust inclination of X-ray beam relative to a horizontal plane for imaging portions such as an upper jaw or a lower jaw so that different portions located above and below, such as a jaw joint positioned above and a top of lower jaw positioned below, are set at the center of radiation field. It is also possible for fine adjustment to combine structures for moving or tilting the chin rest 4c, for providing the above-mentioned patient frame 4b and lift frame 4f as different components, and for shifting the position of the X-ray generator 6 relative to the patient frame 4b or the chin rest 4c.

Figure 2:
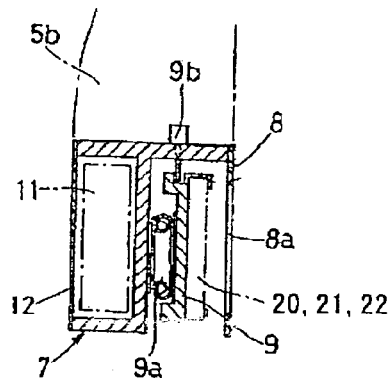
FIG. 2 is a sectional view of an X-ray detector.

The X-ray detector 7 has a shield plate 8 having secondary slits 8a in correspondence to the primary slits and an adjustment mechanism therefor. The shield plate 8 opposes to the X-ray generator 6, and a cassette holder 9 is provided behind the shield plate 8. The secondary slits 8a include a longitudinal slit for panorama imaging (for narrow beam) and a rectangular slit for CT imaging (for wide beam). The cassette holder 9 is supported with a sliding bearing 9a as shown in FIG. 2 to move horizontally in a direction perpendicular to the paper plane on which FIG. 2 is shown, and a motor 9b is mounted for moving the cassette holder 9. In the cassette holder 9, a film cassette 21 including an X-ray film, a digital sensor cassette 22 for panorama imaging including an electric X-ray detector or a digital sensor cassette 20 for CT imaging can be mounted. The X-ray detector 7 has a connector 14 for connection with a digital sensor cassette. The cassette holder 9 is supported to be movable horizontally with a sliding mechanism not shown, and the motor 9b moves the cassette. The X-ray detector 7 has a controller 11 and an operation panel 12 provided at a plane opposite to the X-ray generator. The controller 11 includes printed circuit boards on which various electric circuits are formed. The operation panel 12 (FIG. 7) has various switches and a liquid crystal display device. Further, the controller 11 includes various circuits necessary for a digital cassette sensor and for a two-dimensional sensor cassette.

Figure 3:
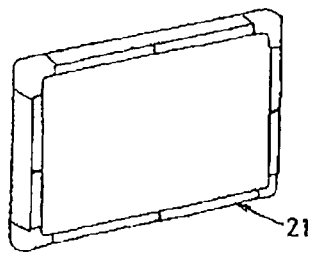
FIG. 3 is a perspective view of a film cassette.

The panorama X-ray imaging apparatus may be a film X-ray imaging apparatus or a digital X-ray imaging apparatus. FIG. 3 shows, as an example, a prior art film cassette 21 used for a film X-ray imaging apparatus wherein an X-ray film or an intensifier is set changeably.

Figure 4:
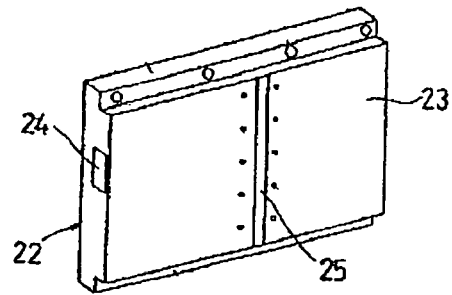
FIG. 4 is a perspective view of a digital sensor cassette.

FIG. 4 shows an example of the digital sensor cassette 22 used in a digital X-ray imaging apparatus. The digital sensor cassette 22 converts the incident X-rays to digital data for pixels arranged in two dimensions. Inside the housing 23, an electric X-ray detector and various circuits connected thereto are mounted. A connector 24 for connection to an external circuit is provided on a side the housing 23. The connector 24 used for connection with an external circuit is usually connected with the connector 14 of the X-ray detector 7 with a cable including power lines and signal lines. It may also be used for connection with an external instrument such as a personal computer. The housing 23 is made of an appropriate material having a necessary rigidity, for example, a metal such as aluminum, or a synthetic resin such as acrylonitrile-butadiene-styrene (ABS) resin. Further, an X-ray receptor 25 is provided at the center of the front plane opposing to the X-ray generator, and it is longitudinal in correspondence to the secondary slit 8a. The receptor 25 is made of a material transparent well to X-rays, but shields visible light rays, such as ABS resin of a dark color, and an electric image detector is mounted at the inside of the slit.

Figure 5:
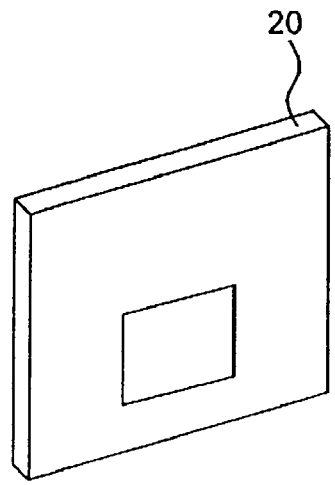
FIG. 5 is a perspective view of a digital sensor cassette for CT imaging.

FIG. 5 shows the digital sensor cassette 20 used as a cassette for X-ray CT scan. The digital sensor cassette 20 uses an X-ray metal oxide semiconductor (MOS) sensor. The X-ray MOS sensor has a three-layer structure, wherein a MOS image sensor layer has photodiodes as pixels, capacitors connected in parallel thereto and MOS transistors for reading connected in series thereto are arranged as a two-dimensional matrix, optical fiber elements for transmitting an optical image are arranged above the MOS image sensor layer, and a scintillator layer above them converts the X-rays to visible light (for example, refer to Japanese Patent laid open Publication JP-A H8-257026/1996). The MOS sensor is used as a two-dimensional X-ray detector for acquiring X-ray projection data for CT imaging of an object. An X-ray image transmitting the object is converted to visible light in the scintillator layer, and the visible light is transmitted through the optical fibers to the MOS image sensor layer to be converted to charges accumulated in the capacitors. On reading, the charges of a pixel selected by an address conversion circuit are converted to a digital value with an analog-to-digital converter.

The digital sensor cassette 20 has two dimensional X-ray detector and various electric circuits therefor in the housing, similarly to the digital sensor cassette 22 shown in FIG. 4. As the electric two-dimensional X-ray detector, besides the above-mentioned X-ray MOS sensor, a CMOS sensor wherein CMOS transistors are used instead of the MOS transistors as switching elements, a thin film transistor (TFT) sensor including thin film transistors, or a frame transfer sensor which performs frame transfer may also be used. Alternatively, an X-ray CCD sensor as a solid state X-ray imaging element may be used. Inside the digital sensor cassette 20, a signal processing device (FIG. 7, 108) including a central processing unit is provided for communication between the two-dimensional X-ray detector and a controller 11. When the cassette 20 is set in the cassette holder 9, signals for controlling X-ray CT imaging are sent to and received from between the two-dimensional X-ray detector and the controller 11. The signal processing device has a driver circuit for driving the two-dimensional X-ray detector, an analog-to-digital converter for converting the digital data, and a storage device for storing the digital data, and it controls the X-ray detection of the two-dimensional X-ray detector based on to instructions from the controller 11.

Figure 6:
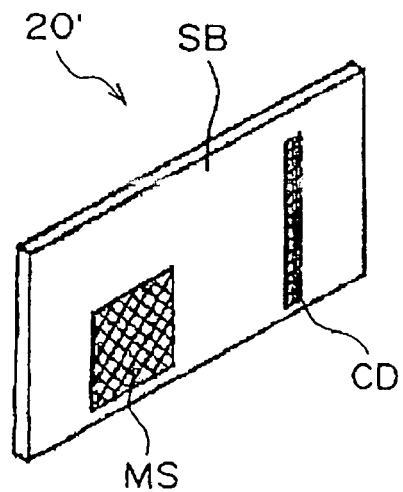
FIG. 6 is a perspective view of another digital sensor cassette.

As shown in FIG. 6, a digital sensor cassette may also be used as a digital sensor cassette for panorama imaging. The digital sensor cassette 20' has two kinds of two-dimensional X-ray detectors, that is, a MOS sensor MS for CT imaging extending in two dimensions and a CCD sensor CD for panorama imaging more longitudinal than the MOS sensor, on a plane of a board SB. The changeover between the two-dimensional X-ray detectors MS and CD is possible, for example, by shifting the cassette holder according to the imaging mode to set the two-dimensional X-ray detector MS, CD at a position for receiving the X-ray radiations. Though not shown, it is also possible to provide the MOS sensor for CT imaging and the CCD sensor CD at both sides of the board BS.

The cassette holder 9 in the X-ray detector 7 has a structure to set the film cassette 21 or the digital sensor cassette 20, 22 without obstruction.

Various techniques may be adopted to instruct a changeover between various imaging modes. For example, an operator instructs a changeover with a switch provided in the cassette. Alternatively, an operator instructs by inserting a pin into a jack provided in the cassette. Alternatively, when a cassette is set, the type of cassette is determined automatically. For example, dips or bumps are formed on a part of an outer plane of a cassette at different positions according to the type of cassette, and they are detected mechanically, optically, or electrically. Alternatively, a limit switch is mounted on a cassette holder for detecting the type of sensor cassette. Alternatively, an IC tag mounted to a sensor cassette is detected. Alternatively, a barcode on a sensor cassette is read. Alternatively, information in an IC chip mounted to the sensor cassette is read. These are examples of devices for responding to the detecting device mechanically, electrically or optically, passively or actively. It is also possible in the side of the X-ray imaging apparatus that an operator pushes a button provided, for example, on the operation panel 12. When the changeover is instructed or detected, the controller 100 changes the contents of the control. The current imaging mode may be displayed in the operation panel or the like.

Figure 7:
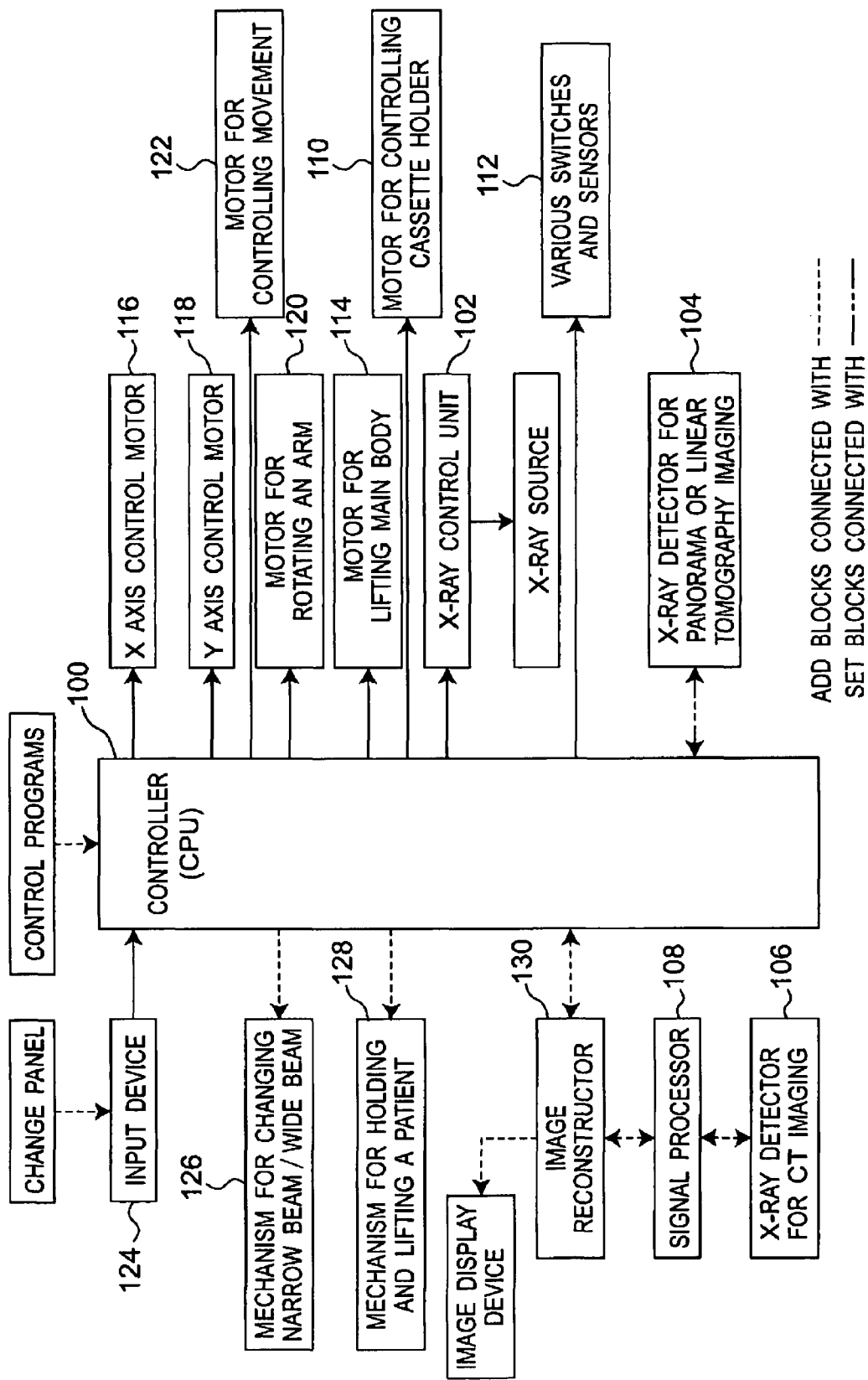
FIG. 7 is a block diagram of a controller.

A controller 100 including a central processing unit (CPU) is included in a support frame 4a. As shown in FIG. 7, an X-ray control unit 102 for controlling an X-ray source in the X-ray generator is connected to the controller 100. Further, the controller 100 is connected selectively to an X-ray detector 104 for panorama imaging or linear tomography imaging in the cassette 20 or 22. The motor 110 for controlling the cassette holder 9 controls the movement of the cassette inserted in the cassette holder 9. Further, the controller 100 receives signals from various switches and sensors 112 provided at various positions in the rotary arm 5. The controller 100 drives a motor 114 for lifting up and down the lift unit, an X-axis control motor 116 and a Y-axis control motor 118 in the X-Y movement mechanism, a motor 120 for rotating the rotary arm 5, and a motor 122 for moving the X-ray generator 6 in a horizontal plane. Further, the controller 100 receives an instruction from an operator with an input device 124 such as buttons in the operation panel to change a cassette or imaging mode. (Alternatively, when it is detected automatically that a cassette is set, the signal thereof is received.) When a cassette is changed, the mechanism 126 is controlled to change the primary slit. Further, the position of the chin rest or the like is moved up or down with the mechanism 128 for moving the patient holder according to the type of imaging. In the case of CT imaging, an image reconstructor 130 as a program for CT image control and image reconstruction calculation is added. The image reconstructor 130 is included in the controller 11 (FIG. 2) and receives X-ray projection data from the two-dimensional X-ray detector 106 in the cassette for CT imaging through the image processor 108. Then, the projection data is calculated to be converted to a distribution of X-ray absorption coefficients of the object, and tomography image data at sections of the object are created. The tomography image data is displayed with the image display device. The controller 100 executes a control program stored in a storage device (not shown) such as a read-only memory based on signals received from various switches and sensors. When the cassette is changed, it is necessary to control the X-ray radiation timing for CT imaging, a radiation field of X-ray beam, and control of the rotary arm according to the change of the cassette, and control programs therefor are also added. In FIG. 7, dashed lines represent blocks added to the apparatus, and two-dots and dash lines represent blocks added selectively to the apparatus.

Figure 8:
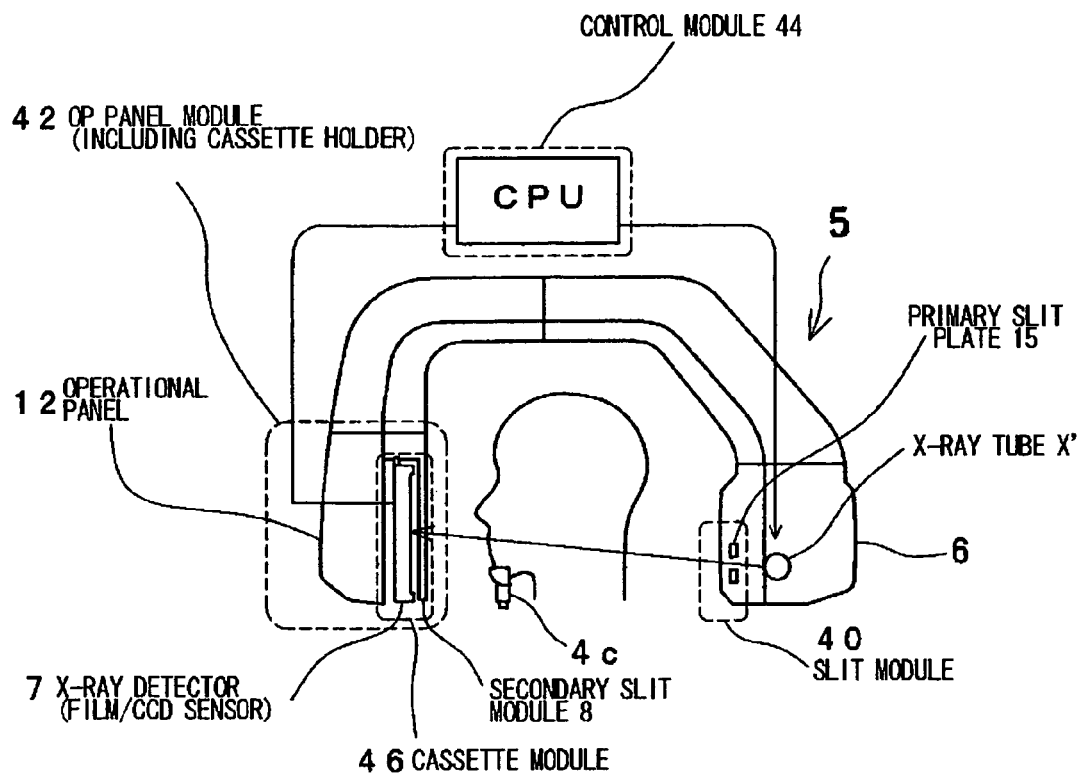
FIG. 8 is a diagram for explaining modifications in the apparatus related to a change of cassette.

With reference to FIG. 8, modification of an X-ray imaging apparatus is explained with reference to the change on the cassette mounted in the cassette holder 9. The X-ray imaging apparatus includes a slit module 40, an operation panel module 42 and a control module 44. The operation panel module 42 includes a cassette module 46. The X-ray generator 6 and the X-ray detector 7 are mounted in the rotary arm 5, as shown in FIG. 1, so as to oppose to each other while interposing an object. When the cassette (or type of imaging) is changed, the shape of radiation field of X-rays radiated from the X-ray generator 6 and the shape on the reception at the X-ray detector are changed according to the specifications of imaging. In the housing including the X-ray detector, the cassette is included in the X-ray detector 7, and at the front of the housing opposing to the X-ray detector 7, a slit module 40 is provided having an X-ray shield plate having primary slits and an adjustment mechanism for changing the shape of the reception of the primary slits. The primary slit plate 15 provided at the front of the X-ray generator 6 has a longitudinal primary slit for panorama imaging and a rectangular slit for CT imaging. When the primary slit is changed, the slit module 40 sets a primary slit in correspondence to the cassette with the driving motor. The cassette module 46 has the X-ray detector 7 (X-ray film, CCD sensor or the like) and secondary slit plates 8 therefor. The cassette module 46 may be changed according to the imaging mode. The operation panel module 42 has the operation panel 12 and the like, besides the cassette module 46. The operation panel module 42 can be formed so as to be replaced entirely. The control module 44 is provided in the support frame 4a and includes the controller 100. When the panorama imaging is changed to CT imaging, the above-mentioned slit module 40, the operation panel module 42 and the control module 44 may be changed or replaced so as to change the shape of radiation field, imaging conditions to be set, trajectory of movement of rotary arm, and control of image data processing.

Figure 9:
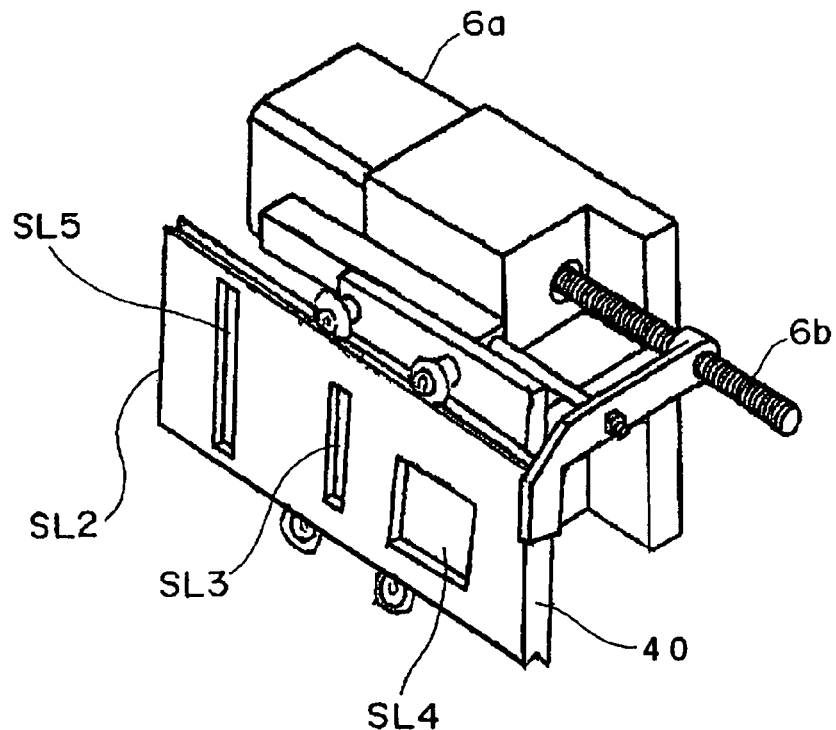
FIG. 9 is a sectional view of a mechanism for setting a primary slit.
Figure 10:
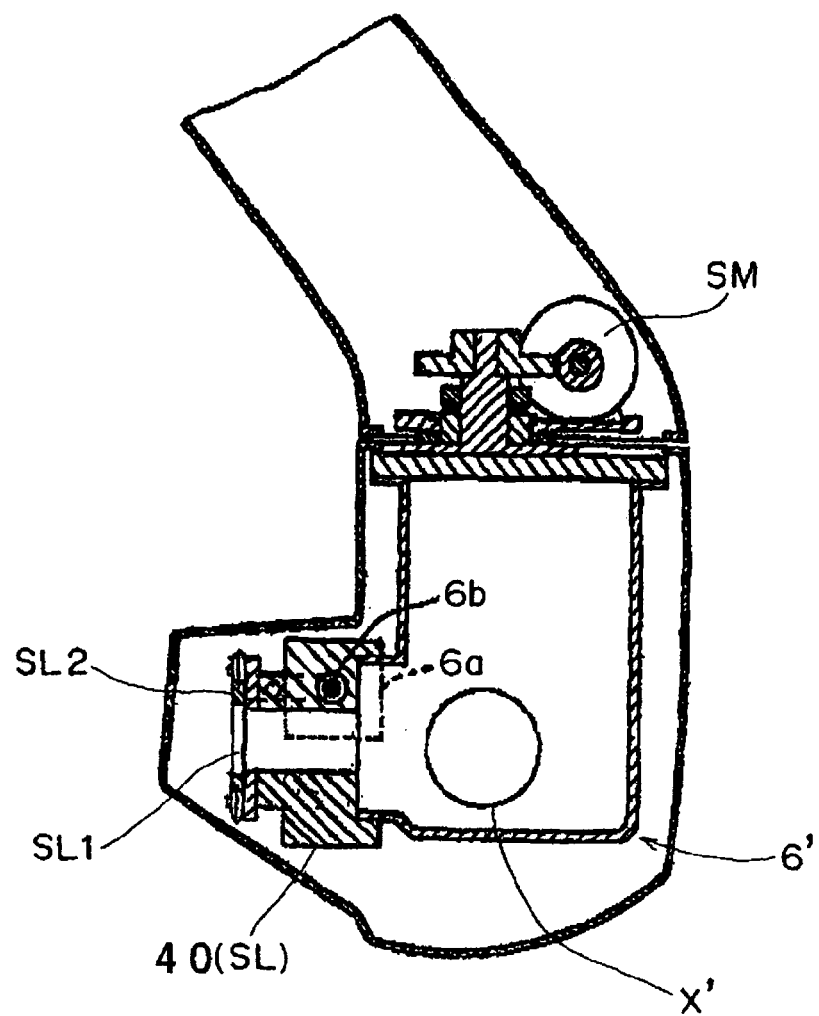
FIG. 10 is a perspective view of the mechanism for setting a primary slit.

FIGS. 9 and 10 show examples of setting of primary slit. When the cassette (type of imaging) is changed, the shape of radiation field of X-rays radiated from the X-ray generator 6 and the shape of the reception at the X-ray detector are changed according to the imaging mode. An X-ray source X' including an X-ray tube is set in the housing 6' including the X-ray generator 6, and the slit module (SL) 40 including the X-ray shield plate including the primary slits SL1 and the mechanism 6b for adjusting the shape of the primary slits are arranged at the front plane of the housing facing the X-ray detector. The primary slit plate SL2 at the front plane of the X-ray generator 6 has a longitudinal slit SL3 for panorama imaging, a rectangular slit SL4 for CT imaging and a long slit SL5 for cephalo imaging. When the cassette is changed, the driving motor 6a in the slit module 40 sets a primary slit SL1 in correspondence to the cassette.

On the other hand, the X-ray detector 7 is integrated with the secondary slit plate (arm cover) which is the shield plate 8 for changing the shape of reception (radiation field) and faces the X-ray generator 6. Therefore, the secondary slit is also changed as the cassette is changed. Alternatively, the secondary slit is set independently of the cassette. In a modified example, the shield plate having a plurality of secondary slits is used, and the secondary slit is selected according to the change of the cassette.

Figure 11:
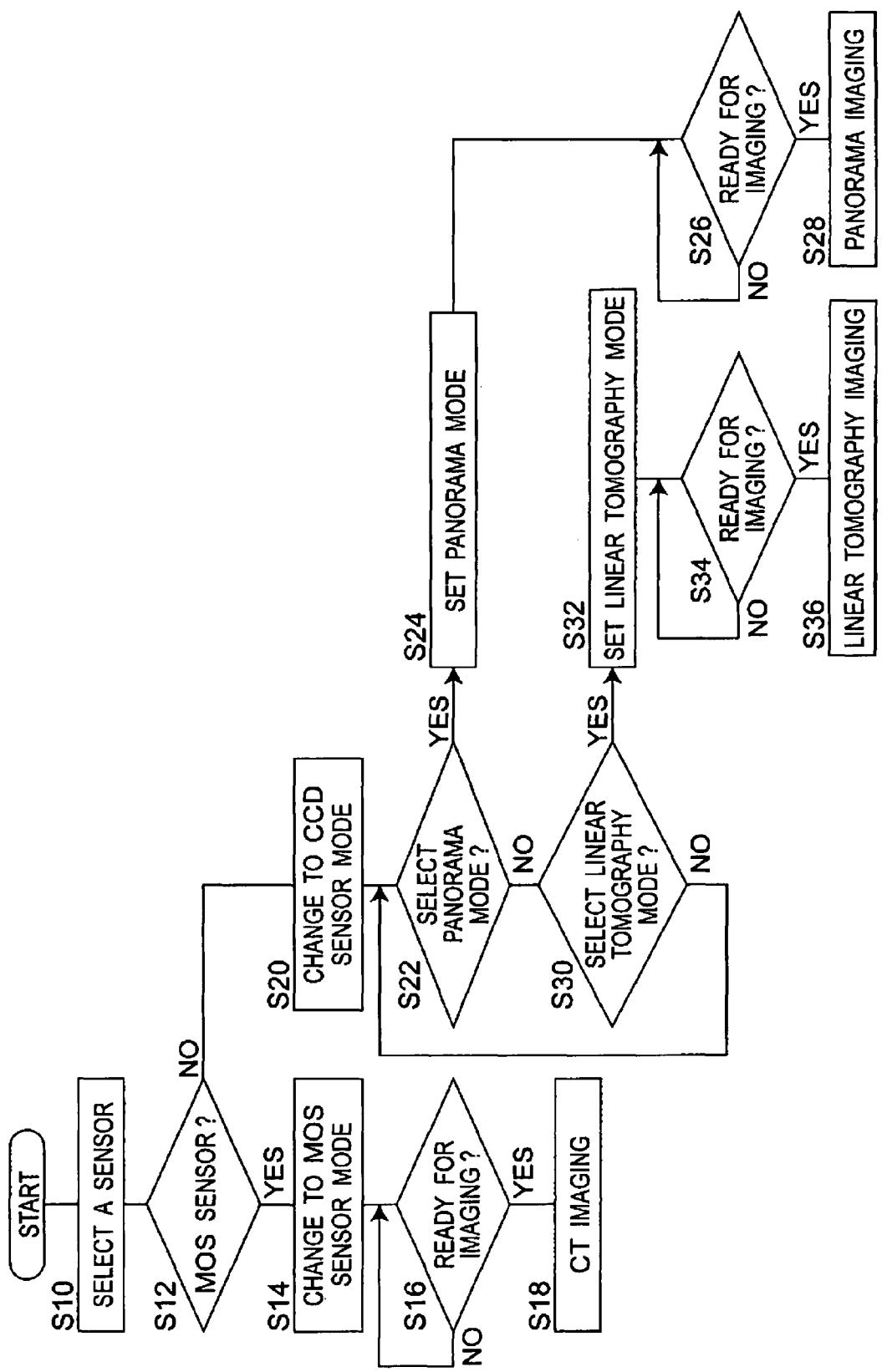
FIG. 11 is a flowchart for changing the control.

The control module (such as a firmware) 44 including the controller 100 in the support frame 4a is changed according to the imaging type to change the contents of the control (refer to FIG. 11).

Further, in a modified embodiment, the housing (the operation panel module 42) at the side of X-ray detector including the cassette holder and the operation panel 12 can be made changeable as a whole. In this case, a part of the software control of the controller 100 may be performed by the controller 11 in the housing. The programs for the software control include programs for controlling the X-ray radiation timing, radiation field of X-ray beam, rotary arm and the like.

The controller 132 shown in FIG. 7 includes the above-mentioned programs. Therefore, the cassette, the secondary slit, the control programs and the operation panel are changed by changing the entire housing. In this case, the operation panel module 42 which is a unit for CT imaging includes the controller for X-ray radiation timing for CT imaging, radiation field of X-ray beam generated by the X-ray generator and the control of the rotary arm, besides the digital sensor cassette for CT imaging having the two-dimensional X-ray detector for acquiring X-ray projection data for CT imaging of an object.

FIG. 11 shows a flowchart for changing the control in the controller 100. When an instruction for selecting a sensor is received or selection of the sensor is detected (S10), the process branches according the instruction or detection (S12). If the sensor selected or detected is a MOS sensor (YES at S12), the apparatus is changed to MOS sensor mode (S14). When the apparatus becomes ready for imaging (YES at S16), CT imaging is performed (S18). If the sensor is not a MOS sensor (NO at step S12), the apparatus is changed to CCD sensor mode (S20). For the CT imaging, the X-ray generator 6 generates X-rays towards the X-ray MOS sensor cassette 20, while the rotary arm having the X-ray generator 6 and the X-ray MOS sensor is rotated around a rotary axis at the center of an object for the imaging.

When panorama imaging is selected or detected (YES at step S22), the apparatus is changed to panorama mode (S24). When the apparatus becomes ready for imaging (YES at S26), panorama imaging is performed (S28). When panorama X-ray imaging is performed, the patient's head is fixed at a predetermined position on the patient's frame 4b, as is known well, and a film cassette 21 including an X-ray film is set in the cassette holder 9. Next, X-rays are generated by the X-ray generator 6 towards the X-ray detector 7. The rotary arm is rotated while moving the rotation center along a predetermined trajectory and moving the cassette holder 9 integrated with the film cassette 21 in a horizontal direction at a predetermined speed. This movement is performed with the motor 9b mounted in the cassette holder 9, and its direction is generally perpendicular to the X-ray beam radiated from the X-ray generator 6 to the X-ray detector 7.

When linear tomography imaging is selected (YES at step S30), the apparatus is set to linear tomography mode (S32). When the apparatus becomes ready for imaging (YES at S34), linear tomography imaging is performed (S36). When the imaging is performed with a film, the X-ray generator 6 generates an X-ray beam towards the film cassette 21, and the X-ray generator 6 and the cassette holder 9 having the film cassette 21 are rotated for imaging around a center of a predetermined imaging portion, (tomography section).

In the above-mentioned embodiments, a cassette to be held in the cassette holder 9 is changed. However, various types of cassette or cassette holder may be used. For example, the cassette holder is designed to include two types of cassettes simultaneously in parallel. By extracting a cassette at the side of X-ray generator, the other cassette behind it can be used. In another example, different X-ray sensors are mounted on two planes of a cassette, and s sensor facing the X-ray generator 6 is selected among them according to the inserted situation into the cassette holder.

In the invention, the X-ray generator 6 and the X-ray detector 7 are moved relatively to an object. For example, the object is fixed, while the X-ray generator 6 and the X-ray detector 7 are moved. Alternatively, the latters are fixed while the former is moved. Thus, in the invention, the movement of the X-ray generator 6 and the X-ray detector 7 relative to an object should be understood as the above-mentioned relative movement. For example, in tomography imaging, the X-ray generator and the X-ray detector are rotated relatively to an object. In this case, in an example, the object is fixed, and the X-ray generator and the X-ray detector are rotated. Alternatively, the X-ray detector are fixed, and the object is rotated or moved. It is also possible to combine the rotation or movement of the object with the rotation of the X-ray generator and the X-ray detector. An operation other than rotation should be understood similarly.

Though dental X-ray imaging apparatuses for imaging a dental arch or the like are explained above, needless to say, the unit for X-ray CT imaging according to the invention can be applied in various medical fields such as imaging for otorhinolaryngology or for neck vertebra.

The invention claimed is:

1. A unit for X-ray CT imaging to be set in a panorama X-ray imaging apparatus having a cassette holder wherein a film cassette comprising an X-ray film or a digital sensor cassette comprising an electric X-ray detector for acquiring a panorama image data is set, the panorama X-ray imaging apparatus comprising an X-ray generator and an X-ray detector including the cassette holder, a rotation device comprising a rotation mechanism and a rotary arm, which rotation device rotating the X-ray generator and the X-ray detector while keeping them opposing to each other and interposing an object, wherein the rotation mechanism drives the rotary arm and moves a rotation center of the rotary arm, whereby a panorama tomography image of the object is acquired according to X-ray radiations from the X-ray generator, the unit for X-ray CT imaging comprising:
   a digital sensor cassette for CT imaging to be set in the cassette holder, including a two-dimensional X-ray detector for acquiring X-ray projection data for CT imaging of the object;
   a controller for controlling a timing of X-ray radiation for CT imaging, a radiation field of X-ray beam generated by the X-ray generator, and the rotation mechanism, and controls a position of the rotation center and a size of the radiation field of X-ray beam depending on the panoramic imaging and the CT imaging; and
   an image reconstructor which calculates to convert the X-ray projection data acquired by the two-dimensional X-ray detector to a distribution of X-ray absorption coefficients of the object and creates a tomography image data at sections of the object.

2. The unit for X-ray CT imaging according to claim 1, further comprising:
   a signal processing device which sends and receives signals for X-ray CT imaging between the two-dimensional X-ray detector and the image reconstructor when the digital sensor cassette for CT imaging is set in the cassette holder.

3. The unit for X-ray CT imaging according to claim 1, further comprising a device for changing radiation field of X-ray beam generated by the X-ray generator mounted on the X-ray generator at a side opposing the X-ray detector, and the device sets the radiation field for CT imaging when the digital sensor cassette for CT imaging is set in the cassette holder.

4. The unit for X-ray CT imaging according to claim 1, further comprising a device for responding to the setting of the cassette comprising one of a switch, a jack for inserting a pin, a component to be engaged with a limit switch in the cassette holder, an IC tag, a bar code and an IC tip as a device for responding to the setting of the cassette.

5. The unit for X-ray CT imaging according to claim 1, wherein the two-dimensional detector is a detector including one of a MOS sensor, a CMOS sensor, a TFT sensor, an X-ray solid state imaging element and an FT sensor.

6. The unit for X-ray CT imaging according to claim 1, wherein the digital sensor cassette for CT imaging includes both of the two-dimensional X-ray detector for CT imaging and an X-ray detector for panorama imaging longer than the two dimensional X-ray detector.

7. A unit for X-ray CT imaging to be set in a panorama X-ray imaging apparatus having a cassette holder wherein a film cassette including an X-ray film or a digital sensor cassette comprising an electric X-ray detector for acquiring a panorama image is mounted, the panorama X-ray imaging apparatus comprising an X-ray generator, an X-ray detector including the cassette holder interposing an object and opposing to each other, and a rotary device which rotates the X-ray generator and the X-ray detector while keeping them opposing to each other and interposing the object, whereby a panorama tomography image of the object is acquired according to X-ray radiations from the X-ray generator, the unit for X-ray CT imaging comprising:
   a digital sensor cassette for CT imaging to be set in the cassette holder, including a two-dimensional X-ray detector for acquiring X-ray projection data for CT imaging of the object;
   an image reconstructor which calculates to convert the X-ray projection data acquired by the two-dimensional X-ray detector to a distribution of X-ray absorption coefficients of the object and creates a tomographic image data of sections of the object; and
   an image processor which sends and receives signals for X-ray CT imaging between the two-dimensional X-ray detector and the image reconstructor when the digital sensor cassette for CT imaging is set in the cassette holder.

8. The unit for X-ray CT imaging according to claim 7, further comprising a device for changing radiation field of X-ray beam generated by the X-ray generator mounted on the X-ray generator at a side opposing the X-ray detector, and the device sets the radiation field for CT imaging when the digital sensor cassette for CT imaging is set in the cassette holder.

9. The unit for X-ray CT imaging according to claim 7, further comprising a device for responding to the setting of the cassette comprising one of a switch, a jack for inserting a pin, a component to be engaged with a limit switch in the cassette holder, an IC tag, a bar code and an IC tip as a device for responding to the setting of the cassette.

10. The unit for X-ray CT imaging according to claim 7, wherein the two-dimensional detector is a detector including one of a MOS sensor, a CMOS sensor, a TFT sensor, an X-ray solid state imaging element and an FT sensor.

11. The unit for X-ray CT imaging according to claim 7, wherein the digital sensor cassette for CT imaging includes the two-dimensional X-ray detector for CT imaging and an X-ray detector for panorama imaging longer than the two dimensional X-ray detector.

12. An X-ray imaging apparatus comprising:
   an X-ray generator and an X-ray detector including a cassette holder, wherein a film cassette comprising an X-ray film or a digital sensor cassette comprising an electric X-ray detector for imaging a panorama image is mounted;
   a rotation device comprising a rotation mechanism and a rotary arm, which rotation device rotating the X-ray generator and the X-ray detector relative to an object while keeping them opposing to each other, wherein the rotation mechanism drives the rotary device and moves a rotation center of the rotary arm; and
   a unit for X-ray CT imaging comprising:
      a digital sensor cassette for CT imaging to be set in the cassette holder, including a two-dimensional X-ray detector for acquiring X-ray projection data for CT imaging of the object;
      a controller for controlling a timing of X-ray radiation for CT imaging, a radiation field of X-ray beam generated by the X-ray generator, and the rotation mechanism, and controls a position of the rotation center and a size of the radiation field of X-ray beam depending on the panoramic imaging and the CT imaging; and
      an image reconstructor which calculates to convert the X-ray projection data acquired by the two-dimensional X-ray detector to a distribution of X-ray absorption coefficients of the object and creates a tomography image data at sections of the object.

13. A unit for X-ray CT imaging to be set in a panorama X-ray imaging apparatus, the panorama X-ray imaging apparatus comprising an X-ray generator and an X-ray detector which comprises an operation panel module used for panoramic imaging including a cassette holder wherein a film cassette comprising an X-ray film or a digital sensor cassette comprising an electric X-ray detector for acquiring a panorama image data is set, a rotation device comprising a rotation mechanism and a rotary arm, the rotation device rotating the X-ray generator and the X-ray detector while keeping them opposing to each other and interposing an object, wherein the rotation mechanism drives the rotary arm and moves a rotation center of the rotary arm, whereby a panorama tomography image of the object is acquired according to X-ray radiations from the X-ray generator, the unit for X-ray CT imaging comprising:
   another operation panel module used as a unit for X-ray CT imaging including a cassette holder, wherein the operation panel module used for panoramic imaging is replaced with the other operation panel module;
   a digital sensor cassette for CT imaging to be set in the cassette holder, including a two-dimensional X-ray detector for acquiring X-ray projection data for CT imaging of the object;
   a controller for controlling a timing of X-ray radiation for CT imaging, a radiation filed of X-ray beam generated by the X-ray generator, and the rotation mechanism, and controls a position of the rotation center and a size of the radiation filed of X-ray beam depending on the panoramic imaging and the CT imaging; and
   an image reconstructor which calculated to convert the X-ray projection data acquired by the two-dimensional X-ray detector to a distribution of X-ray absorption coefficients of the object and creates a tomography image data at sections of the object.

14. An X-ray imaging apparatus comprising:
   an X-ray generator and an X-ray detector which comprises an operation panel module used for panoramic imaging including a cassette holder wherein a film cassette comprising an X-ray film or a digital sensor cassette comprising an electric X-ray detector for acquiring a panorama image data is mounted;
   a rotation device, comprising a rotation mechanism and a rotary arm, which rotates the X-ray generator and the X-ray detector relative to the object while keeping them opposing to each other and interposing an object;
   wherein the rotation mechanism drives the rotary device and moves a rotation center of the rotary arm; and
   a unit for X-ray CT imaging comprising:
      another operation panel module used as a unit for X-ray CT imaging including a cassette holder, wherein said operation panel module used for panoramic imaging is replaced with the other operation panel module;

a digital sensor cassette for CT imaging to be set in the cassette holder, including a two-dimensional X-ray detector for acquiring X-ray projection datat for CT imaging of the object;

a controller for controlling a timing of X-ray radiation for CT imaging, a radiation field of X-ray beam generated by the X-ray generator, and the rotation mechanism, and controls a position of the rotation center and a size of the radiation field of X-ray beam depending on the panoramic imaging and the CT imaging; and an image reconstructor which calculates to convert the X-ray projection data acquired by the two-dimensional X-ray detector to a distribution of X-ray absorption coefficients of the object and creates a tomography image data at sections of the object.

* * * * *